United States Patent [19]

Luceyk et al.

[11] 4,038,194
[45] July 26, 1977

[54] BLOOD FILTER UNIT

[75] Inventors: Alfred Robert Luceyk, Santa Paula; Herman Charles Mouwen, Ventura, both of Calif.; Steven Louis Weinberg, East Brunswick, N.J.

[73] Assignees: Johnson & Johnson, New Brunswick, N.J.; Purolator, Inc., Del.

[21] Appl. No.: 646,775

[22] Filed: Jan. 6, 1976

Related U.S. Application Data

[63] Continuation of Ser. No. 462,454, April 19, 1974, abandoned.

[51] Int. Cl.² .................. B01D 27/00; B01D 35/00
[52] U.S. Cl. ............................. 210/436; 210/448; 210/493 B; 210/497 R; 210/DIG. 23
[58] Field of Search ............... 210/436, 446, 448, 493, 210/497, DIG. 23

[56] References Cited

U.S. PATENT DOCUMENTS

| | | | |
|---|---|---|---|
| 3,042,571 | 7/1962 | Jackson | 210/493 B |
| 3,458,050 | 7/1969 | Cooper | 210/493 X |
| 3,591,010 | 7/1971 | Pall et al. | 210/493 |
| 3,701,433 | 10/1972 | Krakauer et al. | 210/436 |

*Primary Examiner*—Frank A. Spear, Jr.
*Assistant Examiner*—Richard W. Burks

[57] ABSTRACT

A blood filter unit comprising an assembly for supporting a filter cartridge, a filter cartridge, and a housing for the assembly and cartridge. The assembly for supporting the cartridge comprises a permeable cylindrical core with a bottom member and a top cap. The filter media, in the form of a cartridge, is disposed about the periphery of the core and extends between the bottom member and top cap. The core contacts the media only at intermittent areas spaced longitudinally and circumferentially about the core. The core, media and walls of the housing are tapered with respect to each other.

7 Claims, 2 Drawing Figures

BLOOD FILTER UNIT

This is a continuation application of our copending application Ser. No. 462,454 filed Apr. 19, 1974 and now abandoned.

BACKGROUND OF THE INVENTION

The present invention is directed to the filtration of blood. In medical, hospital and surgical treatments today there are a number of instances when blood is filtered; e.g. during blood transfusions, dialysis treatments, and in the extracorporeal blood circuits used during some surgical procedures.

The filters used in the filtration of blood must meet stringent requirements. The blood filter must be sterile and hence should be readily sterilizable. The filter must be efficient and remove the unwanted materials from the blood without removing the desired materials or having any detrimental effect on the desirable materials in the blood. The filter must be constructed to prevent gas bubbles in the blood flowing to the patient. The filter must not contain any foreign material that might be released into the blood being filtered.

In view of the problems involved in cleaning and sterilizing reusable filters, disposable filters have gained considerable acceptance in the filtration of blood. The disposable blood filters generally comprise a number of parts, such as the housing, the core for holding the media, and the filter media or cartridge itself. These parts must be assembled and sealed or secured together to form a filter unit and the unit cleaned, flushed, and sterilized prior to being placed into use. After a single use, the filter is discarded. This means the filter cannot be expensive yet must meet critical specifications.

SUMMARY OF THE INVENTION

We have discovered an improved unit for filtering blood. Our new blood filter may be readily flushed and made medically clean prior to its final assembly. Our new unit is easily assembled and positively sterilized by steam, gas or radiation sterilization. Also, our new filter does not damage the blood being filtered and has excellent gas bubble elimination characteristics. Our new filter has reduced blocking characteristics and improved flow characteristics.

In accordance with the present invention, our new unit for filtering blood comprises an assembly for supporting a filter cartridge, a filter cartridge and a housing for the assembly and cartridge. The housing and the assembly are fixedly securable to each other so as to be leak-proof. In a preferred embodiment, the housing threads on to the assembly as will hereinafter be described.

The assembly for supporting the filter cartridge comprises a permeable cylindrical core. A top cap is attached to one end of the core to seal this end of the core along with filter media positioned about the periphery of the core. On the other end of the core, there is a bottom member which extends outwardly from the core for supporting the media. The construction is such as to leave the center of the core open to act as the outlet for the filtered blood. The outer edge of the bottom member may be provided with threads for attaching the assembly to the housing. The filter media extends between the top cap and bottom member about the circumference of the core. The core and media are in contact only at a minimum of intermittently spaced-apart areas with the areas of contact spaced longitudinally and circumferentially about the core. In one embodiment of our new filter unit, the distance between the media and the core is greatest adjacent the bottom member and the distance between the media and the core is the least adjacent the top cap.

In a preferred embodiment of our unit for filtering blood, the housing has a tapered cylindrical form. The housing is smaller in diameter at its upper portion and larger in diameter at its lower portion. The distance between the media and inside wall of the housing is smallest adjacent the bottom member with the distance between media and inside wall of the housing the largest adjacent the top cap.

The housing has a blood inlet and a vent in its uppermost portion to allow air to escape.

The filter media used may be in the form of a convoluted cartridge. In this pleated configuration, the pleats run the length of the cartridge. We have discovered when using such a pleated cartridge, it is preferred that the pleats have a greater density at the top of the filter than at the bottom of the filter; i.e., the pleats are closer together at the top of the filter than at the bottom of the filter. It is believed that this configuration aids in allowing the material being removed from the blood to easily settle to the bottom of the filter and not get caught in the pleats and block off portions of the filter.

BRIEF DESCRIPTION OF THE DRAWINGS

The present invention will be further described in conjunction with the accompanying drawings wherein.

DETAILED DESCRIPTION OF THE PRESENT INVENTION

Figures 1, 2:
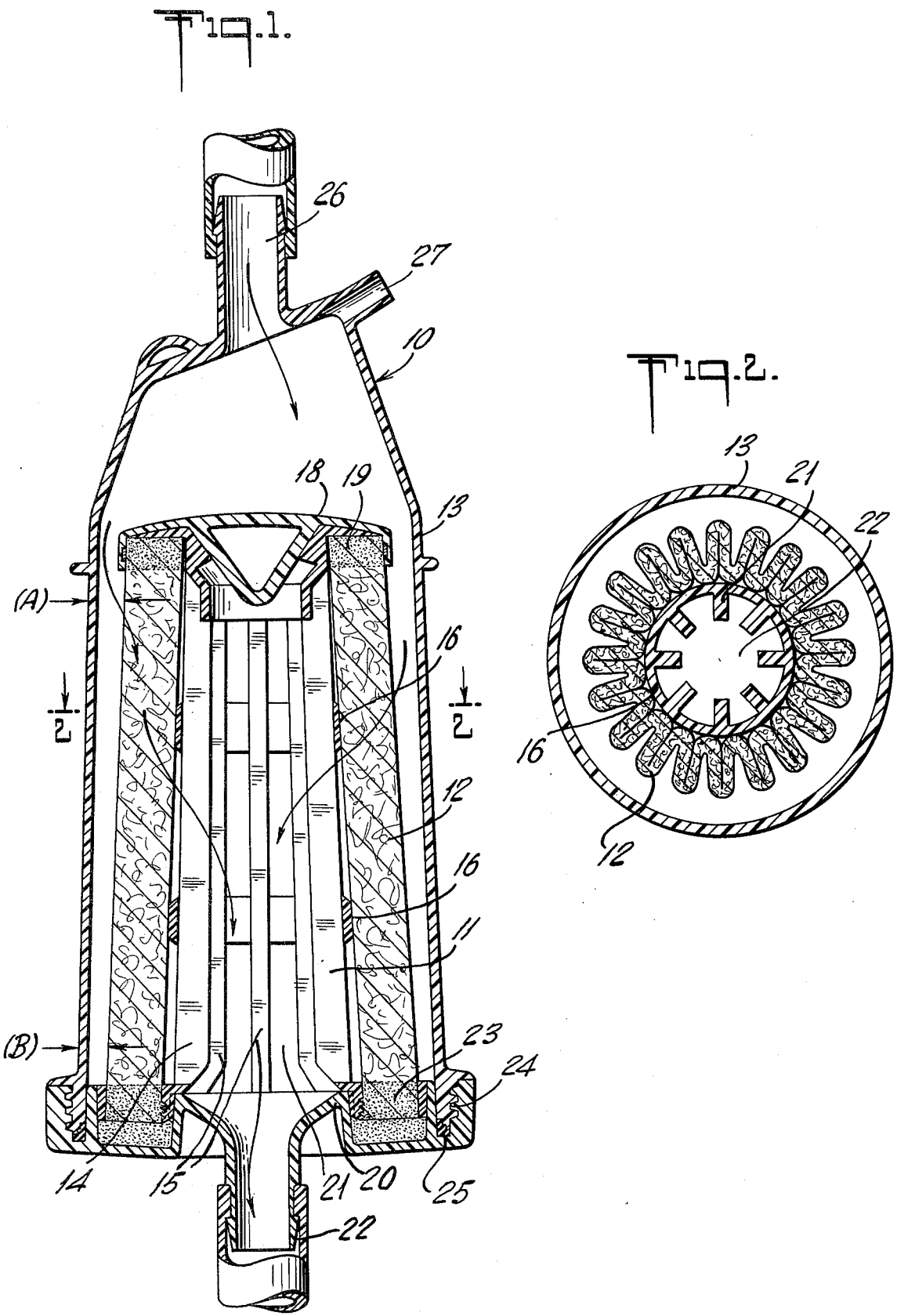
FIG. 1 is a cross-sectional view of a blood filter unit in accordance with the present invention.
FIG. 2 is a cross-sectional view taken along line 2—2 of FIG. 1.

Referring to the drawings in FIGS. 1 and 2, there is shown a blood filter unit 10 comprising the assembly for supporting a filter cartridge 11, the cartridge 12, and the housing 13. The assembly 11 comprises a core 14 which is cylindrical in shape and is permeable. The core comprises a number of longitudinal struts 15 held in spaced-apart relationship by a plurality of annular rings 16.

It is preferred that the core be conical in shape for ease of manufacture and ease of assembly of the filter unit.

The filter media is in the form of a cartridge 12 which has a convoluted configuration and encircles the entire periphery of the core. The media contacts the core only at those portions of the flutes which contact the outwardly extending rings so that contact between core and media is only at intermittently spaced-apart areas which are spaced longitudinally and circumferentially about the core. The contact between solid portions of the core and filter media is kept to a minimum to reduce blockage of the filter area. By using vertical pleats in the media and horizontal annular rings as the only contacting supporting structure, it is insured that contact between core and media is kept to a minimum and only at discrete, intermittently spaced-apart areas. This construction reduces harmful effects on blood caused by obstructions in the flowing blood stream as these obstructions have been reduced to a minimum.

Covering the top of the core and the filter media is the top cap 18. The media is sealed to the top cap by a hot melt adhesive 19. Attached to the bottom of the core is the bottom member 20 which extends outwardly from the periphery of the core. This construction leaves the center of the core 21 open to form the outlet 22 for the filter. The media is sealed in the bottom member by hot melt adhesive 23. The outer edge of the bottom member is threaded 24 and carries a suitable gasket 25 so that the bottom member may be securely attached to the filter housing 13 and a tight, leak-proof seal produced at the gasket.

The above-described construction allows the entire assembly and cartridge to be flushed and medically cleaned before it is inserted in the housing, sealed and sterilized. The assembly and cartridge may be flushed from both directions to insure that any foreign particles or impurities that might be present are removed and eliminate the possibility of foreign material being present in this portion of the filter when it is placed in use.

In use, the blood being filtered flows from the outside of the filter media, through the media, through the core and out the center outlet of the core. It may be theorized that the space between the media and the core and the minor contact between the two reduces the deleterious effects on blood. The smaller the area of filter media that is blocked by the core, the less the pressure drop during the filtering operation. Also the above-described configuration of the space between the media and the core aids in eliminating entrapment of gas in the filtered blood.

Surrounding the filter cartridge is the housing 13. The bottom open end of the housing is threaded so it may be joined to the bottom member of the assembly. The housing is cylindrical in shape and in a preferred embodiment of the present invention; the side walls of the housing are tapered as shown in FIG. 1, to improve the flow characteristics of the filter and aid in the evacuation of gas or air entrapped by the filter. At the top of the filter is an inlet 26 for the incoming blood. The inlet is shown substantially in the center of the top portion of housing though it could be off-set or moved to the side of the housing as desired. Also at the uppermost point of the filter, there is a vent 27 to allow air to escape from the filter as it is being filled and to allow any gases removed from the blood to continue to escape during filtration.

In use, the blood enters the top center inlet 26 and flows down over the top cap 18 down along the side walls of the housing to fill up the housing forcing the air to escape through the top vent 27. The blood flows through the filter media to the space between the core and the media and the filtered blood passes through the permeable core and out the center bottom outlet 22. This flow is shown by the arrows in FIG. 1.

A preferred spacing between the inside walls of the housing and the media is shown in FIG. 1. The spacing (A) is greater at the upper portion of the media than the spacing (B) at the bottom of the media. This configuration improves the ease with which gas is allowed to escape from the housing and aids in degassifying the blood being filtered. This configuration also improves the fluid flow characteristics of the blood and reduces turbulence or undesirable agitation of the blood which may be harmful.

Also the configuration eliminates secondary flow zones within the filter, that is zones where blood might sit and not move for periods of time. The configuration allows for the continual movement of blood throughout the filter. A quiet zone in the filter may cause sedimentation and be harmful and disrupt or reduce the filtering efficiency of the unit. Also, this configuration unexpectedly eliminates the problem of "unloading" of the filter media. In many blood filter units, there is a problem with the media starting to become blocked. This blocking will increase the pressure drop across the media. If conditions are right, at certain times, the filter will unload or pass portions of the material which may be damaging to the patient. Unexpectedly, the relative shape of the inside housing wall to the upstream filtering surface of the media as has been described and as shown in FIG. 1 greatly reduces this problem of "unloading".

The filter housing and support assembly may be made from various plastic or metal materials provided the material is inert to the action of blood. The material may be opaque, translucent or transparent as desired. Suitable materials are polyolefins, such as polypropylene, polyethylene, the butadiene-styrene polymers, polycarbonates, and similar materials.

With the two-piece assembly as described each piece may be thoroughly and completely flushed to make it medically clean and remove any foreign particles that might remain in the parts as a result of their manufacture or their handling prior to being assembled. The pieces after being thoroughly cleaned and flushed are assembled as described and the unit sterilized by gas sterilization or radiation sterilization.

The media used in our improved filter is either depth type media such as the synthetic fiber felts, synthetic foams and the like, or sieve type media such as woven polyester fabrics, woven nylon fabrics and the like. The specific media used will be determined by the type of operation in which the filter unit will be used.

In a specific embodiment, the filter media is in a pleated configuration with the pleats running the length of the media. As may be seen in the drawings, the number of pleats used in the cartridge 12 are uniform, however, the distance between pleats is greater at the bottom end cap 20 than at the top cap 18. This means the spacing between pleats is tapered with adjacent pleats diverging from each other from the top cap to the bottom cap. Filtered material which may be caught between pleats at the top portion will readily settle to the bottom of the filter and reduce the propensity for the media to become blocked.

Having thus described the invention, it should be understood that many variations and modifications may be made to the invention without departing from the invention itself. The invention is only limited by the scope of the claims appended hereto.

What is claimed is:

1. A unit for filtering blood comprising an assembly for supporting a filter cartridge, a filter cartridge, and a housing for said assembly and cartridge, said housing having a tapered cylindrical form with the smaller diameter end of said housing having an inlet for the blood to be filtered and an air vent, said housing and said assembly being fixedly securable to each other, said assembly for supporting a filter cartridge comprising a permeable cylindrical core, a top cap attached to one end of the core to seal said end, a bottom member attached to the opposite end of the core and extending outwardly from the periphery of the core leaving the center of the core open to act as the filter outlet, a filter cartridge comprising filter media extending between said top cap and said bottom member and about the circumference of said core, said media being sealed to the top cap and the bottom member, said core and said media in contact only at discrete, intermittent areas spaced longitudinally and circumferencially about the core and the distance between the housing and the filter media being uniformly increased from bottom member to the top cap and the area of the internal opening of the filter media being steadily increased from the top cap to the bottom member, whereby the uniformity of filter media utilization is increased.

2. A unit for filtering blood according to claim 1 wherein the filter media is in a pleated configuration with the pleats extending the length of the filter cartridge and the density of pleats is greater adjacent the top cap than adjacent the bottom member.

3. A unit for filtering blood according to claim 1 wherein the filter media is a woven fabric in a pleated configuration with the pleats extending the length of the cartridge.

4. A unit for filtering blood according to claim 1 wherein the filter media is nonwoven fabric in a pleated configuration with the pleats extending the length of the cartridge.

5. A unit for filtering blood according to claim 1 wherein the permeable cylindrical core has a conical configuration.

6. A unit for filtering blood according to claim 1 wherein the blood inlet is substantially in the center of the top of the housing and said housing has an air vent at its uppermost point.

7. A unit for filtering blood according to claim 1 wherein the media is sealed to the top cap and bottom member by hot melt adhesive.

* * * * *